United States Patent
Lefevre et al.

(10) Patent No.: US 9,220,684 B2
(45) Date of Patent: Dec. 29, 2015

(54) HIGH-FLUIDITY AND NON-CAKING PULVERULENT CRYSTALLINE MALTITOL COMPOSITION

(75) Inventors: Philippe Lefevre, Haverskerque (FR); Jose Lis, La Gorgue (FR); Guillaume Ribadeau-Dumas, Verlinghem (FR)

(73) Assignee: ROQUETTE FRERES, Lestrem (FR)

( * ) Notice: Subject to any disclaimer, the term of this patent is extended or adjusted under 35 U.S.C. 154(b) by 482 days.

(21) Appl. No.: 12/936,578

(22) PCT Filed: Apr. 7, 2009

(86) PCT No.: PCT/FR2009/050591
§ 371 (c)(1), (2), (4) Date: Oct. 6, 2010

(87) PCT Pub. No.: WO2009/136056
PCT Pub. Date: Nov. 12, 2009

(65) Prior Publication Data
US 2011/0027355 A1    Feb. 3, 2011

(30) Foreign Application Priority Data
Apr. 8, 2008   (FR) .................................... 08 52352

(51) Int. Cl.
| | |
|---|---|
| *A23L 1/236* | (2006.01) |
| *A61K 9/14* | (2006.01) |
| *A23G 1/40* | (2006.01) |
| *A23G 3/42* | (2006.01) |
| *A23G 4/10* | (2006.01) |

(52) U.S. Cl.
CPC ... *A61K 9/14* (2013.01); *A23G 1/40* (2013.01); *A23G 3/42* (2013.01); *A23G 4/10* (2013.01); *A23L 1/2364* (2013.01)

(58) Field of Classification Search
None
See application file for complete search history.

(56) References Cited

U.S. PATENT DOCUMENTS

| | | | |
|---|---|---|---|
| 4,408,041 A | | 10/1983 | Hirao et al. |
| 4,976,972 A | * | 12/1990 | Patel et al. ........................ 426/3 |
| 5,547,689 A | | 8/1996 | Ribadeau-Dumas et al. |
| 5,580,601 A | | 12/1996 | Ribadeau-Dumas et al. |
| 2004/0052897 A1 | | 3/2004 | Beauregard et al. |
| 2005/0112260 A1 | * | 5/2005 | Abraham et al. ............. 426/548 |
| 2005/0118316 A1 | | 6/2005 | Ueno et al. |

FOREIGN PATENT DOCUMENTS

| | | |
|---|---|---|
| EP | 0662285 A1 | 7/1995 |
| EP | 0664960 A1 | 8/1995 |
| EP | 1738657 A2 | 1/2007 |
| EP | 1787993 A1 | 5/2007 |
| WO | WO 2005115342 A1 * | 12/2005 |

OTHER PUBLICATIONS

International Search Report, dated Feb. 1, 2010, from corresponding PCT application.

* cited by examiner

*Primary Examiner* — Nissa Westerberg
(74) *Attorney, Agent, or Firm* — Young & Thompson

(57) ABSTRACT

A pulverulent crystalline maltitol composition, is characterized in that it has a laser volume mean diameter between 10 and 150 μm; in that it has a maltitol content between 80 and 99.9% by weight; in that at least 50% by weight of its particles flow through a sieve having a cut-off threshold of 2000 μm according to a test A1; in that at least 35% by weight of its particles flow through a sieve having a cut-off threshold of 2000 μm according to a test A2; and in that it includes from 0.1 to 20% by weight of at least one water-insoluble anti-caking agent, the anti-caking agent having a hygroscopicity, determined according to the test B, between 2.5 and 25%. This composition is not subject to caking, and finds applications in the food and pharmaceutical fields.

16 Claims, No Drawings

HIGH-FLUIDITY AND NON-CAKING PULVERULENT CRYSTALLINE MALTITOL COMPOSITION

The present invention relates to a pulverulent crystalline maltitol composition, the fluidity of which is preserved. This crystalline maltitol powder thus has the particular characteristic of not being subject to caking. The composition according to the invention advantageously has a fine particle size.

In the sense of the invention, the expression "pulverulent crystalline maltitol composition" is understood to mean a powder containing crystalline maltitol.

In the sense of the invention, the expression "crystalline maltitol" is also understood to mean the product of the conventional crystallization of an aqueous solution of maltitol or any other maltitol in crystalline form.

4-O-alpha-D-glucopyranosyl-D-sorbitol, commonly known as maltitol, is a polyol obtained industrially by hydrogenation of maltose.

It is of considerable interest owing to the fact that it is more chemically stable, less calorific and has a lower glycaemic index than sucrose, yet advantageously possesses organoleptic properties very similar to those of this sugar.

Moreover, maltitol possesses the particular characteristic that it is not cariogenic, for which reason it has already found a variety of industrial applications, especially in the food and pharmaceutical industries, especially in the fields of chewing gum, table-top sweeteners and chocolate.

For a very long time, maltitol was only marketed in the form of low-concentration syrups, or in the form of amorphous, impure powders.

It was only at the beginning of the 1980s that the company HAYASHIBARA described the production of anhydrous maltitol crystals for the first time in its patent U.S. Pat. No. 4,408,041.

Previously, this polyol had always been considered to be a non-crystallizable product.

This erroneous assumption actually originated from the fact that the crystallization of maltitol from a supersaturated solution is not as easy to control as in the case of other polyols, such as mannitol or erythritol for example.

The techniques known as "starch sugar" techniques on the one hand and as crystallization in water techniques on the other hand, are today almost the only processes used industrially.

The products thus obtained have, however, a very variable crystallinity, and are not all particularly well suited to certain applications such as those of chewing gum or chocolate.

These crystalline products are not completely satisfactory either when, for example, it is desired to use maltitol to replace sucrose or lactose in dry pharmaceutical forms such as gelatin capsules and medicinal products of the following types: powders to be dissolved, tablets and pulverulent nutritional preparations to be diluted.

This is also the case when it is desired to produce the same type of substitution in sweet foods such as powdered drinks, desserts, cake preparations or chocolate or vanilla powders for breakfast.

It is observed for these particular applications, especially for the pseudo-crystalline maltitol powders obtained by the "starch sugar" technique, and to a lesser degree for the crystalline maltitol powders obtained by crystallization in water, that these powders have one or more failings such as, in particular, those of:
not flowing easily;
being subject to agglomeration or caking; and
only dissolving very slowly in water.

The specialists in the field of polyol crystallization are therefore tasked with developing maltitol compositions that do not have the failings, especially of flow and of caking, that the known maltitol powders have.

Generally, the polyols proposed in the form of pulverulent products are stored and distributed in double packaging that combines an inner bag made from a plastic with a bag made of Kraft paper or with a corrugated cardboard box or else in flexible containers known as "big bags". The packaging of the crystalline maltitol powder currently sold makes use of one or other of these packaging methods.

Despite these precautions, commercial maltitol powders tend to agglomerate into large clusters, and are therefore sensitive to caking. This tendency to caking will be even greater when the maltitol powder has a fine particle size.

The crystalline maltitol powders thus caked during storage raise a large number of problems, not only through the serious handling difficulties that ensue therefrom (transfer and unpacking, milling and putting back into solution, etc.), but also by significantly impacting the yield of these operations.

A certain number of solutions have been proposed for overcoming these difficulties:
adding anti-caking agents such as magnesium stearate or talc to the maltitol powder;
either sliding small sachets containing a silica gel type desiccant between the outer packaging material and the inner bag or inside the latter, or opting for a double-lined outer packaging material, between the inner and outer linings of which a hygroscopic substance will have been previously inserted.

The first method is not however taken up by the specialists in the field of handling maltitol powders since it is considered that:
the introduction of impurities into the maltitol powder may detract from its commercial value;
the organoleptic qualities risk being impaired; and
the regulatory constraints forbid the use of such additives in certain applications.

As regards the possible use of a method of packaging with a desiccant, the risk of a possible contamination of the packaged product by the desiccant cannot be dismissed.

To remedy this situation, in its patent application EP 1.787.993, the company IOWA proposes treating the crystalline maltitol downstream from the production techniques conventionally known from the prior art.

TOWA thus recommends using various means taking into consideration:
the balance between the moisture inside the particles and that present on their surface;
the balance between the moisture of the powder particles (both inside and on the surface) and the ambient moisture; and also
stabilizing the surface of the powder.

In patent application EP 1.787.993, the method consists of a contact treatment consisting in introducing the crystalline maltitol powder, and air that has been brought to a temperature of 20° C. to 50° C. and having a relative humidity of 5 to 50%, into a dryer for five to fifty hours, at a space velocity of 2 to 15 $h^{-1}$.

However, it is observed that this method applies to maltitol powders that are characterized by their very high maltitol concentration (i.e. of more than 99.5%; for instance, LESYS, which has a maltitol content of 99.7 wt %).

Furthermore, although the maltitol powders described in this patent application are said to have a particle size below 500 µm (qualified as the proportion of powder that passes through the JIS sieve with a mesh size of 0.50 mm), the standard crystalline maltitol powders tested, of LESYS type, sold by TOWA, or of MALTISORB® type, sold moreover by the Applicant company, in fact have a mean diameter greater than 200 μm, and may thus be qualified as large particle size crystalline maltitol powder.

It is well known by a person skilled in the art that the behaviour of polyol powders in general, and of maltitol in particular, especially as regards their flowability, changes dramatically as a function of their particle size: a powder having a mean diameter of 400 to 500 μm will not have the same behaviour as a maltitol powder having a mean diameter of 50 to 200 μm.

The result of this is that the solution recommended by TOWA in fact only applies to high-purity crystalline maltitol powders that have a large particle size.

From the aforegoing, it ensues that there remains an unmet need to provide a crystalline maltitol composition of fine particle size, for example between 10 and 150 μm; and that has a variable, for example from 80 to 99.9 wt %, maltitol content, the fluidity of which is preserved and which thus has the particular characteristic of not being subject to caking.

It is meritorious of the Applicant company to propose a technical solution that goes against the technical prejudice according to which it is strongly advised not to use an anti-caking agent in the preparation of a pulverulent crystalline maltitol composition.

The Applicant company recommends using an anti-caking agent. This anti-caking agent must, however, be chosen from a particular class of anti-caking agents, more particularly characterized by:
  their insolubility in water;
  their ability to absorb water; and
  preferably, their fine particle size.

The invention consequently relates, firstly, to a pulverulent crystalline maltitol composition, characterized in that:
  it has a laser volume mean diameter between 10 and 150 μm;
  it has a maltitol content between 80 and 99.9 wt %;
  at least 50 wt % of its particles flow through a sieve having a cut-off threshold of 2000 μm according to a test A1; and
  at least 35 wt % of its particles flow through a sieve having a cut-off threshold of 2000 μm according to a test A2.

The values of the particle size distribution are determined on a LS 13-320 type laser diffraction particle size analyser from BECKMAN-COULTER, equipped with its (dry route) powder dispersion module, by following the operating guide and the manufacturer's specifications.

The operating conditions of hopper screw speed and of vibration intensity of the dispersion chute are determined so that the optical concentration is between 4% and 12%, ideally 8%.

The measurement range of the LS 13-320 type laser diffraction particle size analyser is from 0.04 μm to 2000 μm. The results are calculated in % by volume, and expressed in μm.

The particle size distribution curve also makes it possible to determine the value of the volume mean diameter (arithmetic mean) D(4,3) (laser volume mean diameter).

The pulverulent crystalline maltitol composition according to the invention thus has a laser volume mean diameter D(4,3) between 10 and 150 μm, preferably 20 to 120 μm.

According to one embodiment, the pulverulent crystalline maltitol composition according to the invention has a laser volume mean diameter between 50 and 90 μm; preferably between 60 and 80 μm.

According to another embodiment, the pulverulent crystalline maltitol composition according to the invention has a laser volume mean diameter between 15 and 50 μm; preferably between 20 and 40 μm.

The pulverulent crystalline maltitol composition according to the invention has a maltitol content between 80 and 99.9 wt %; preferably between 85 and 99.9 wt %; preferably between 90 and 99.9 wt %; preferably between 95 and 99.9 wt %.

The anti-caking nature of the pulverulent crystalline maltitol composition according to the invention is determined according to an accelerated ageing test A.

This test uses low-density polyethylene sachets with internal dimensions of 10 cm ×5 cm, which are obtained by heat-sealing low-density polyethylene films having a thickness of 100 μm along three sides.

Introduced into these sachets are 100 g of the powder to be tested, then these sachets are hermetically heat-sealed.

In a first variant, known as an "unpressurized" variant (test A1), the sachets are laid flat, separately, in a climatic chamber.

In a second variant, known as a "pressurized" variant (test A2), a 2 kg weight is placed on the sachets, which corresponds to a pressure of 400 kg/m$^2$.

Over 7 days the sachets undergo a succession of cycles of:
  3.5 hours at 23° C. in 83% relative humidity (or RH);
  0.5 h of transition;
  3.5 hours at 40° C. in 92% RH; and
  0.5 h of transition.

At the end of these 7 days, the sachets are opened and poured over a sieve having a mesh of 2000 μm, vibrated for 10 seconds over its trademark FRITSCHT™ Pulverisette Type 00.502 support.

The amplitude of the vibration is set to 5 and is stable.

The result is expressed as the percentage by weight of particles that pass through the 2000 μm sieve.

According to the "unpressurized" test A1, at least 50 wt % of the particles of the composition according to the invention pass through the 2000 μm sieve. According to one preferred embodiment, according to the test A1, at least 60%, preferably at least 65%, preferably at least 70%, preferably at least 75%, preferably at least 80%, preferably at least 85%, preferably at least 90%, preferably at least 95% of the particles of the pulverulent crystalline maltitol composition according to the invention pass through the 2000 μm sieve.

According to the "pressurized" test A2, at least 35 wt % of the particles of the composition according to the invention pass through the 2000 μm sieve. According to one preferred embodiment, according to the test A2, at least 40%, preferably at least 50%, preferably at least 60%, preferably at least 70%, preferably at least 80%, preferably at least 90%, preferably at least 95% by weight of the particles of the pulverulent crystalline maltitol composition according to the invention pass through the 2000 μm sieve.

By way of comparison, as will be exemplified below, a maltitol powder as sold by the Applicant company under the trade name MALTISORB® P90 presents the following results:
  according to the test A1, only 5.2% of the crystalline maltitol particles pass through the 2000 μm sieve; and
  according to the test A2, only 7.4% of the crystalline maltitol particles pass through the 2000 μm sieve.

According to one embodiment, the pulverulent crystalline maltitol composition according to the invention is also characterized by its content of anti-caking agent.

These anti-caking agents are chosen from the anti-caking agents characterized by:
their insolubility in water;
their ability to absorb water; and
preferably, their fine particle size.

More particularly, the pulverulent crystalline maltitol composition according to the invention is then characterized in that it comprises from 0.1 to 20 wt % of at least one water-insoluble anti-caking agent having:
a hygroscopicity, determined at 80% relative humidity according to the test B, between 2.5 and 25%; and
preferably, a laser volume mean diameter below 100 μm.

The water-insoluble nature of the anti-caking agent is determined by its chemical structure. A person skilled in the art is familiar with the soluble or insoluble nature of a compound in water.

The ability of the anti-caking agents to adsorb water is determined according to a test B for measuring the difference in weight expressed in %, between 80% relative humidity and 20% relative humidity at 20° C.

This test consists in evaluating the relative variation in weight of the anti-caking agent when it is subjected to a cycle of relative humidity (known as RH) at 20° C. in equipment manufactured by Surface Measurement Systems™ (London, UK) and known as Dynamic Vapour Sorption Series 1.

This equipment comprises a differential microbalance which makes it possible to quantify the change in weight of a sample relative to a reference (here, the reference cradle of the differential balance is empty) when this sample is subjected to various climatic conditions.

The carrier gas is nitrogen, and the weight of the sample is less than 10 mg.

At the constant temperature of 20° C., each anti-caking agent undergoes the following relative humidity cycle: 5 hours at 20%, climb from 20% to 70% over 30 minutes, hold for 5 hours at 70%, climb from 70% to 80% over 30 minutes, and hold for 5 hours at 80%.

The hygroscopicity at 80% RH is then given by the equation: $(m_{80}-m_{20})/m_{20} \times 110$ expressed in %, where $m_{20}$ is the mass of the sample at the end of the 5 hours at 20% RH and $m_{80}$ is the mass of the sample at the end of the 5 hours at 80% RH.

The anti-caking agents that are used in the pulverulent crystalline maltitol composition according to the invention have a hygroscopicity, determined at 80% relative humidity according to a test B, between 2.5 and 25%.

By way of comparison, other conventionally chosen anti-caking agents, such as magnesium stearate or talc, have a very poor ability to adsorb water; specifically, their hygroscopicity values at 80% RH, measured according to the test B, are between 0.05 and 1.0%.

The anti-caking agents of the pulverulent crystalline maltitol composition according to the invention may also be characterized by their particle size, measured on a LS 13-320 type laser diffraction particle size analyser from BECKMAN-COULTER, equipped with its (dry route) powder dispersion module, by following the operating guide and the manufacturer's specifications, as indicated above.

According to one embodiment, these anti-caking agents have a laser volume mean diameter below 100 μm. Preferably, according to the invention, the anti-caking agent has a laser volume mean diameter below 80 μm, more preferably below 50 μm, more preferably below 40 μm, more preferably below 30 μm, more preferably below 10 μm.

According to one embodiment, the pulverulent crystalline maltitol composition according to the invention comprises from 0.1 to 15%, preferably from 0.1 to 10%, preferably from 0.1 to 5% by weight of anti-caking agent.

According to one preferred method of preparing the pulverulent crystalline maltitol composition according to the invention, the anti-caking agent is chosen from the group composed of fumed silica, sodium aluminosilicate, anhydrous tricalcium phosphate and dehydrated potato starch (especially dehydrated potato starch having less than 12% residual water, preferably having less than 10% residual water, preferably having less than 8% residual water, preferably having 6% residual water), used alone or in combination.

According to a first embodiment of this preferred method, the pulverulent crystalline maltitol composition according to the invention comprises from 0.3 to 3 wt %, preferably around 0.5 to 2 wt % of fumed silica or of sodium aluminosilicate.

According to a second embodiment of this preferred method, the pulverulent crystalline maltitol composition according to the invention comprises from 0.3 to 3 wt %, preferably around 2 wt % of anhydrous tricalcium phosphate.

According to a third embodiment of this preferred method, the pulverulent crystalline maltitol composition according to the invention comprises from 0.5 to 20 wt %, preferably around 5 wt % of dehydrated starch (especially dehydrated potato starch having less than 12% residual water, preferably having less than 10% residual water, preferably having less than 8% residual water, preferably having 6% residual water).

As will be exemplified below, these anti-caking agents satisfy the prerequisite properties relating to:
their insolubility in water;
their ability to absorb water; and
preferably, their fine particle size.

The present invention also relates to the use of at least one such water-insoluble anti-caking agent having:
a hygroscopicity, determined according to the test B, between 2.5 and 25%; and
preferably, a laser volume mean diameter below 100 μm, for the preparation of a pulverulent crystalline maltitol composition.

According to one embodiment, the present invention also relates to the use of at least at anti-caking agent chosen from:
fumed silica;
sodium aluminosilicate;
anhydrous tricalcium phosphate; and
dehydrated potato starch (especially dehydrated potato starch having less than 12% residual water, preferably having less than 10% residual water, preferably having less than 8% residual water, preferably having 6% residual water),
for the preparation of a pulverulent crystalline maltitol composition.

According to one embodiment, the pulverulent crystalline maltitol composition according to the invention is capable of being obtained by mixing:
crystalline maltitol having a laser volume mean diameter between 10 and 150 μm; and
at least one water-insoluble anti-caking agent, said anti-caking agent having a hygroscopicity, determined according to the test B, between 2.5 and 25%, and preferably having a laser volume mean diameter below 100 μm.

According to one embodiment, in the pulverulent crystalline maltitol composition according to the invention, the laser volume mean diameter of the anti-caking agent is smaller than the laser volume mean diameter of the crystalline maltitol.

According to one preferred embodiment, the pulverulent crystalline maltitol composition according to the invention is capable of being obtained by mixing:

crystalline maltitol having a laser volume mean diameter between 50 and 90 µm; preferably between 60 and 80 µm; for example MALTISOR™ P90 sold by the Applicant company; and at least one anti-caking agent as indicated above.

According to another preferred embodiment, the pulverulent crystalline maltitol composition according to the invention is capable of being obtained by mixing:

crystalline maltitol having a laser volume mean diameter between 15 and 50 µm; preferably between 20 and 40 µm; for example MALTISOR™ P35 sold by the Applicant company; and at least one anti-caking agent as indicated above.

The pulverulent crystalline maltitol composition according to the invention is capable of being obtained by employing any method known, moreover, by a person skilled in the art, comprising a step of physical mixing of the two powders.

The invention also relates to the use of a pulverulent crystalline maltitol composition as described above for filling flexible containers, for example "big bags".

Furthermore, the pulverulent composition according to the invention is of use in the food and/or pharmaceutical fields.

Thus, the present invention also relates to the use of a pulverulent crystalline maltitol composition as described above, for the preparation of food compositions, especially confectionery such as chewing gums, chocolates, table-top sweeteners, biscuits, ice creams, powdered drinks, desserts, cake preparations or chocolate or vanilla powders for breakfast; and/or for the preparation of pharmaceutical compositions, especially dry pharmaceutical forms such as gelatin capsules and medicinal products of the following types: powders to be dissolved, tablets and pulverulent nutritional preparations to be diluted.

The invention will be even better understood with the aid of the following examples, which are not intended to be limiting and only instance certain embodiments and certain advantageous properties of the crystalline maltitol powder according to the invention.

EXAMPLES

Example 1

Four pulverulent crystalline maltitol compositions were prepared by physical mixing of a crystalline maltitol powder sold by the Applicant company under the trade name MALTISORB® P90, having a volume mean diameter D(4,3) of 69.5 µm, with 4 anti-caking agents:

the fumed silica AEROSIL™ 200, sold by EVONIK-DEGUSSA GmbH;

the sodium aluminosilicate DURAFILL™ 200, sold by W. R. GRACE & Co.;

the anhydrous tricalcium phosphate or TCP, sold by PRAYON S. A.; and the dehydrated potato starch with 6% residual water, sold by the Applicant company under this same name.

These 4 anti-caking agents exhibit the water adsorption and particle size characteristics represented in Table 1 below.

TABLE 1

|  | Hygroscopicity at 80% RH according to test B (%) | Laser D(4,3) volume mean diameter (µm) |
|---|---|---|
| AEROSIL 200 fumed silica | 3.09 | 0.012 |
| DURAFILL 200 sodium aluminosilicate | 5.48 | 4.91 |
| TCP | 3.47 | 7.16 |
| Dehydrated potato starch | 15.06 | 35.96 |

The maltitol powder and anti-caking agent contents of these 4 pulverulent crystalline maltitol compositions according to the invention are presented in Table 2 below.

TABLE 2

|  | Composition "A" | Composition "B" | Composition "C" | Composition "D" |
|---|---|---|---|---|
| MALTISORB ® P90 (wt %) | 98 | 98 | 98 | 95 |
| AEROSIL ™ 200 fumed silica (wt %) | 2 | | | |
| DURAFILL ™ 200 sodium aluminosilicate (wt %) | | 2 | | |
| TCP (wt %) | | | 2 | |
| Dehydrated potato starch (wt %) | | | | 5 |

The compositions "A", "B", "C" and "D" according to the invention have a laser volume mean diameter between 10 and 150 µm.

The anti-caking nature of these 4 pulverulent crystalline maltitol compositions was determined using accelerated ageing test A.

The values obtained are presented in Table 3 below.

TABLE 3

|  | Composition "A" | Composition "B" | Composition "C" | Composition "D" |
|---|---|---|---|---|
| Test A1 Unpressurized accelerated ageing test (%) | 83.9 | 68.7 | 82.3 | 97.6 |
| Test A2 Pressurized accelerated ageing test (%) | 72.3 | 48.9 | 35.4 | 98.6 |

These results were compared with measurements carried out with anti-caking agents of magnesium stearate type (Mg stearate Ph./Veg from Wiga Pharma GmbH) and talc (Talc extra sup DEC from Talc Luzenac), the water adsorption and particle size parameters of which are given in Table 4 below.

TABLE 4

|  | Hygroscopicity at 80% RH according to test B (%) | Laser D(4,3) volume mean diameter (μm) |
|---|---|---|
| Magnesium stearate | 0.86 | 11.1 |
| Talc | 0.08 | 19.9 |

The measurements carried out according to the accelerated ageing test A on the two control compositions "E" (99% MALTISORB® P90 and 1% magnesium stearate) and "F" (98% MALTISORB® P90 and 2% of Talc) are presented in Table 5 below.

TABLE 5

|  | Composition "E" | Composition "F" |
|---|---|---|
| Test A1 Unpressurized accelerated ageing test | 8.5% | 3.5% |
| Test A2 Pressurized accelerated ageing test | 6.9% | 8.2% |

The pulverulent crystalline maltitol compositions according to the invention therefore have remarkable flow properties.

Example 2

A pulverulent crystalline maltitol composition was prepared by physical mixing of a crystalline maltitol powder sold by the Applicant company under the trade name MALTISORB® P90, having a volume mean diameter D(4,3) of 77.8 μm, with an anti-caking agent, the dehydrated potato starch which has a water content of 6.0%. Finally, this pulverulent mixture comprised 95% of maltitol powder and 5% of dehydrated starch. The composition had a laser volume mean diameter between 10 and 150 μm.

Starting from the same batch of MALTISORB® P90, a physical mixture was prepared with magnesium stearate, so as to obtain a pulverulent mixture comprising 98% of maltitol powder and 2% of magnesium stearate. The composition had a laser volume mean diameter between 10 and 150 μm.

With each of these two physical mixtures and the initial batch of MALTISORB® P90, three 66S-type flexible containers containing a polyethylene bag having a thickness of 100 μm, were filled with 800 kg of powder.

These three containers were sealed at the same time and in an identical manner. Next, these three flexible containers were placed side by side on wooden palettes, and were stored for one year in the same unheated and uninsulated warehouse. They were therefore subjected to the variations in temperature and in humidity linked to the natural changing of the climate, but also to the customary variations between the periods of day and night.

After having been stored for one year the flexible containers were taken to an unloading installation suitable for this type of container and the ease with which they were emptied was observed:

For the MALTISORB® P90 powder alone: after opening the unloading chute, no powder flowed. The product was completely agglomerated and it will be impossible to empty this flexible container.

For the mixture with magnesium stearate: after opening the unloading chute, the product flowed very poorly, and a large number of large clumps rapidly blocked the unloading chute. Several manual interventions will be necessary in order to completely empty the container, with a consequent loss of product. The product recovered will not be able to be used as is in its final application since it has too many hard clumps and since its particle size is very different from its initial particle size.

For the mixture with dehydrated starch: after opening the unloading chute, the powder flowed very rapidly and uniformly. The powder recovered had a few small, very friable clumps and its particle size was not very different from the original. The mixture will be able to be used as is without any problem in its final application.

The invention claimed is:

1. A puiverant crystalline maltitol composition, comprising:
   a maltitol content between 80 and 99.9 wt %;
   at least 50 wt % of particles of the composition flow through a sieve having a cut-off threshold of 2000 μm according to a test A1, said test A1 comprising the steps of:
   introducing 100g of said composition into a low-density polyethylene sachet with internal dimensions of 10 cm ×5 cm, which are obtained by heat-sealing low-density polyethylene films having a thickness of 100 μm along three sides,
   hermetically heat-sealing the sachet comprising said composition,
   laying the sachet flat in climatic chamber over seven days and subjecting the sachet to a succession of four cycles:
   (i) 3.5 hours at 23° C. in 83% relative humidity (or RH),
   (ii) 0.5 h of transition,
   (iii) 3.5 hours at 40° C. in 92% RH, and
   (iv) 0.5 h of transition, and
   opening the sachet at the end of the seven days and pouring said composition over a sieve having a mesh of 2000μm, vibrating for 10 seconds at an amplitude setting of 5over an agate pocket and ball mill, wherein said wt % of particles are those that pass through the 2000 μm sieve;
   at least 35 wt % of particles of the composition flow through a sieve having a cut-off threshold of 2000 μm according to a test A2, said test A2 being identical to said test A1 except that the sachet pressurized by placing a 2 kg weight on the sachet during said seven days in said climatic chamber;
   from 0.1 to 20 wt % of an anti-caking agent selected from the group consisting of fumed silica, sodium aluminosilicate, anhydrous tricalcium phosphate and dehydrated potato starch, and mixtures thereof, said anti-caking agent having a hygroscopicity at 80% RH, determined according to the test B, between 2.5 and 25%, said test B comprising the steps of:
   subjecting a less than 10 mg sample of said anti-caking agent to a cycle of relative humidity (PI) at 20° C., with nitrogen as a carrier gas, in equipment comprising a differential microbalance which makes it possible to quantify a change in weight of a sample relative to a reference when said sample is subjected to various climatic conditions, said cycle comprising:
   (i) 5 hours at 20% RH,
   (ii) an increase from 20% to 70% RH over 30 minutes,
   (iii) holding for 5 hours at 70% RH,
   (iv) increasing from 70% to 80% RH over 30 minutes, and
   (v) holding for 5 hours at 80%,
   wherein hygroscopicity at 80% RH is according to the following equation: $(m_{80}-m_{20})/m_{20} \times 100$ expressed in %, where $m_{20}$ is the mass of the sample at the end of the 5 hours at 20% RH and $m_{80}$ is the mass of the sample at the end of the 5 hours at 80% RH; and wherein said composition has a laser volume mean diameter between 10 and 150 µm.

2. The composition according to claim 1, wherein the anti-caking agent has a laser volume mean diameter below 100 µm.

3. The composition according to claim 1, wherein the composition has a laser volume mean. diameter between 50 and 90 µm.

4. The composition according to claim 1, wherein the composition has a laser volume mean diameter between 15 and 50 µm.

5. The composition according to claim 1, wherein the composition is capable of being obtained by mixing:

crystalline maltitol having a laser volume mean diameter between 10 and 150 µm; and an anti-caking agent selected from the group consisting of fumed silica, sodium aluminoscate, anhydrous tricalcium phosphate and dehydrated potato starch, and mixtures thereof, said anti-caking agent having a hygroscopicity at 80% RH, determined according to the test B, between 2.5 and 25%, and having a laser volume mean diameter below 100 µm.

6. The composition according to claim 5, wherein the crystalline maltitol has a laser volume mean diameter between 50 and 90 µm.

7. The composition according to claim 5, wherein the crystalline maltitol has a laser volume mean diameter between 15 and 50 µm.

8. The composition according to claim 1, wherein the composition comprises from 0.3 to 3 wt % of fumed silica or of sodium alumdnosilicate.

9. The composition according to claim 1, wherein the composition comprises from 0.3 to 3 wt % of anhydrous tricalcium phosphate.

10. The composition according to claim 1, wherein the composition comprises from 0.5 to 20 wt % of dehydrated starch having 6% residual water.

11. A method of preparing a pulverulent crystalline maltitol composition comprising:

mixing crystalline maltitol and an anti-caking agent selected from the group consisting of fumed silica, sodium aluminosilicate, anhydrous tricalcium phosphate and dehydrated potato starch, and mixtures thereof, said anti-caking agent having:

a hygroscopicity at 80% RH, determined according to the test B, between 2.5 and 25%, said test B comprising the steps of:

subjecting a less than 10 mg sample of said anti-caking agent to a cycle of relative humidity (RH) at 20° C., with nitrogen as a. carrier gas, in equipment comprising a differential microbalance which makes it possible to quantify a change in weight of a sample relative to a reference when said sample is subjected to various climatic conditions, said cycle comprising:

(i) 5 hours at 20% RH,
(ii) an increase from 20% to 70% RH over 30minutes,
(iii) holding for 5 hours at 70% RH,
(iv) increasing from 70% to 80% RH over 80minutes, and
(v) holding for 5 hours at 80%, wherein hygroscopicity at 80% RH is according to the following equation : $(m_{80}-m_{20})/m_{20}\times 100$ expressed in %, where $m_{20}$ is the mass of the sample at the end of the 5 hours at 20% RH and $m_{80}$ is the mass of the sample at the end of the 5 hours at 80% RH; and a laser volume mean diameter below 100 µm.

12. The composition according to claim 1, packaged in a flexible container.

13. A method of preparing a food or pharmaceutical composition comprising using the composition according to claim 1 in the manufacture of a food or pharmaceutical composition, wherein the food composition is a confectionery selected from the group consisting of chewing gums, chocolates, table-top sweeteners, biscuits, ice creams, powdered drinks, desserts, cake preparations and chocolate or vanilla powders for breakfast; and the pharmaceutical composition is a dry pharmaceutical form selected from the group consisting of gelatin. capsules, medicinal powders to be dissolved, medicinal tablets and pulverulent nutritional preparations to be diluted.

14. The composition according to claim 2, the composition has a laser volume mean diameter between 50 and 90 µm.

15. The composition according to claim 2, the composition has a laser volume mean diameter between 15 and 50 µm.

16. The composition according to claim 2, wherein the composition is capable of being obtained by mixing:

crystalline maltitol having a laser volume mean diameter between 10 and 150 µm; and an anti-caking agent selected from the group consisting of fumed silica, sodium aluminosilicate, anhydrous tricalcium phosphate and dehydrated potato starch, and mixtures thereof, said anti-caking agent having a hygroscopicity at 80% RH, determined according' to the test B, between 2.5 and 25%, and having a laser volume mean diameter below 100 µm.

* * * * *